(12) United States Patent
Makino

(10) Patent No.: US 12,108,929 B2
(45) Date of Patent: Oct. 8, 2024

(54) ELECTRONIC ENDOSCOPE SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 310 days.

(21) Appl. No.: 17/604,918

(22) PCT Filed: Aug. 31, 2020

(86) PCT No.: PCT/JP2020/032939
§ 371 (c)(1),
(2) Date: Oct. 19, 2021

(87) PCT Pub. No.: WO2021/065286
PCT Pub. Date: Apr. 8, 2021

(65) Prior Publication Data
US 2022/0211250 A1 Jul. 7, 2022

(30) Foreign Application Priority Data

Sep. 30, 2019 (JP) .................................. 2019-180236

(51) Int. Cl.
*A61B 1/045* (2006.01)
*A61B 1/00* (2006.01)
(Continued)

(52) U.S. Cl.
CPC .... *A61B 1/000094* (2022.02); *A61B 1/00006* (2013.01); *A61B 1/000095* (2022.02);
(Continued)

(58) Field of Classification Search
None
See application file for complete search history.

(56) References Cited

U.S. PATENT DOCUMENTS

2008/0118117 A1\* 5/2008 Gauldie ................. A61B 6/032
382/128
2015/0181185 A1 6/2015 Ikemoto et al.
(Continued)

FOREIGN PATENT DOCUMENTS

JP 2013-202138 10/2013
JP 2014-018333 2/2014
(Continued)

OTHER PUBLICATIONS

International Search Report issued in WIPO Patent Application No. PCT/JP2020/032939, dated Nov. 10, 2020, along with an English translation thereof.

*Primary Examiner* — Eileen M Adams
(74) *Attorney, Agent, or Firm* — GREENBLUM & BERNSTEIN P.L.C.

(57) ABSTRACT

An electronic endoscope system is provided with an electronic endoscope, a processor provided with a still image acquisition unit that acquires a part of a moving image imaged by the electronic endoscope as a still image, an association processing unit that associates place information regarding an imaging place of living tissue in a lumen with the still image, and a recording unit, a monitor, and an input operation device that transmits a capture instruction for acquiring the still image from the moving image to the still image acquisition unit in response to an operation of determining one place out of a plurality of places in the lumen set in advance as a selected place as a trigger, and further transmits information of the selected place to the association processing unit as the place information regarding the imaging place during an imaging period of the moving image.

9 Claims, 8 Drawing Sheets

(51) Int. Cl.
*A61B 1/06* (2006.01)
*G06T 1/00* (2006.01)

(52) U.S. Cl.
CPC ............ *A61B 1/045* (2013.01); *A61B 1/0684* (2013.01); *G06T 1/00* (2013.01)

(56) References Cited

U.S. PATENT DOCUMENTS

| | | | |
|---|---|---|---|
| 2017/0265723 A1* | 9/2017 | Yamaya | ............ A61B 1/00096 |
| 2018/0279866 A1 | 10/2018 | Makino | |
| 2021/0219817 A1 | 7/2021 | Koizumi et al. | |
| 2021/0259515 A1 | 8/2021 | Makino | |

FOREIGN PATENT DOCUMENTS

| | | |
|---|---|---|
| JP | 2018-047067 | 3/2018 |
| WO | 2017/057680 | 4/2017 |
| WO | 2020/066670 | 4/2020 |
| WO | 2020/066807 | 4/2020 |
| WO | 2020/070818 | 4/2020 |

* cited by examiner

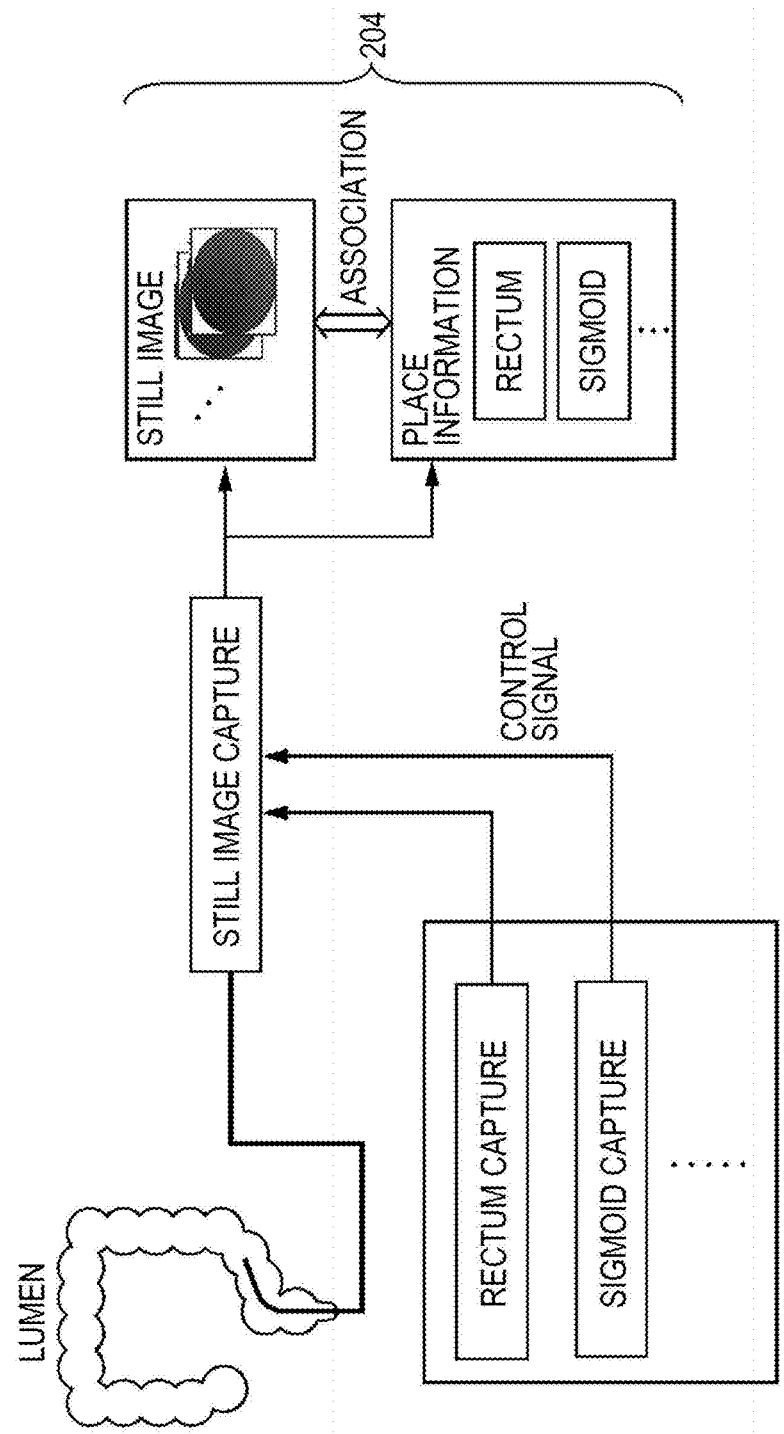

ELECTRONIC ENDOSCOPE SYSTEM

TECHNICAL FIELD

The present invention relates to an electronic endoscope system that acquires a still image from a moving image of living tissue in an organ.

BACKGROUND ART

In a lesion area in living tissue, there are various levels of severities from an inflammation with a thinned mucosal layer of the living tissue that exhibits redness to an ulcer in which the mucosal layer and a lower layer thereof are partially lost. For example, an ulcer part of a lesion of ulcerative colitis (UC) includes white moss and purulent mucus to be white, and an inflammation part causes edema and exhibits redness due to easiness in bleeding. Such lesion area may be imaged to be observed and inspected with an endoscope system.

An endoscope system images a moving image, so that a still image is acquired from the moving image according to an instruction of an operator and recorded to be stored in a memory and the like; however, in a case where it is not clear where in an organ the still image is imaged, it is often impossible to specify a place of the lesion in the organ. For this reason, it is preferable to associate the still image with information of an imaging place.

For example, an electronic endoscope in which optical sensors for acquiring information of a position where a color endoscopic image is imaged are provided at regular intervals on an outer periphery of an insertion portion is known (Patent Literature 1).

Since the optical sensors are provided at regular intervals in the insertion portion of the electronic endoscope, the optical sensor provided in a portion inserted into the organ (digestive tract) of the insertion portion does not detect external light, and the optical sensor provided in a portion not inserted into the organ (digestive tract) detects the external light, so that it is possible to acquire information of a position (insertion length) of a distal tip of the electronic endoscope by determining a distribution length of the optical sensors not detecting light as a length of the insertion portion inserted into the organ (digestive tract).

CITATION LIST

Patent Literature

Patent Literature 1: JP 2014-18333 A

SUMMARY OF INVENTION

Technical Problem

In this manner, in the above-described technology, since a dedicated sensor for position detection is separately provided in the insertion portion of the electronic endoscope, a device configuration becomes complicated, and since the dedicated sensor is provided, an outer diameter of the insertion portion of the electronic endoscope becomes large, and a large burden is imposed on a subject, which is not preferable. Therefore, it is preferable to efficiently acquire information of an imaging place with an existing system without using the dedicated sensor.

Therefore, an object of the present invention is to provide an electronic endoscope system capable of efficiently acquiring information of an imaging place of a still image without providing a dedicated sensor in the electronic endoscope and associating the information with the still image when acquiring the still image from a moving image of living tissue imaged in a lumen.

Solution to Problem

One aspect of the present invention is an electronic endoscope system configured to acquire a still image from a moving image of living tissue imaged in a lumen. The electronic endoscope system is provided with:

an electronic endoscope configured to image an image of living tissue in a lumen as a moving image;

a processor provided with a still image acquisition unit configured to acquire a part of an imaged moving image of the living tissue as a still image by an instruction, a recording unit configured to record the still image, and an association processing unit configured to associate place information regarding an imaging place of the living tissue in the lumen with the still image;

a monitor configured to display the moving image and the still image; and an input operation device configured to transmit a capture instruction for acquiring the still image from the moving image to the still image acquisition unit in response to an operation of determining one place out of a plurality of places in the lumen set in advance as a selected place as a trigger, and further transmit information of the selected place to the association processing unit as the place information regarding the imaging place during an imaging period of the moving image.

Preferably, the input operation device is provided with a plurality of buttons to which information of different places in the lumen is assigned so as to be distinguishable from each other, and is configured to determine the selected place by pressing of one of the buttons, and make the pressing of one of the buttons the trigger for transmission of the capture instruction.

Preferably, in each of the buttons, a name of a place in the lumen, a distance from an open end of the lumen, or identification information specifying the place of the lumen is set as information of the place in the lumen.

Preferably, the input operation device is a keyboard, the button is a key of the keyboard, and
the processor is provided with a display control unit configured to control to display information in which the information of the place in the lumen set in the key is associated with a number, a character, or a symbol set in the key on the monitor.

Preferably, the button is a button in which the name of the place in the lumen, distance information from the open end of the lumen, or the identification information is displayed on a touch panel as the information of the place in the lumen.

Preferably, the input operation device is provided with a selection operation device configured to select the selected place, and a determination operation device configured to determine the selected place that is selected, and is configured to transmit the capture instruction to the still image acquisition unit in response to a determination operation by the determination operation device as a trigger.

Preferably, the association processing unit is configured to write the place information regarding the imaging place in the still image.

Preferably, the processor is provided with an information correction unit configured to overwrite the place information regarding the imaging place already associated with the still image with information of one place selected from the plurality of places in the lumen set in advance as the place information regarding the imaging place outside an imaging period of the moving image for a still image to which the place information regarding the imaging place is associated as erroneous information.

Preferably, the input operation device is provided with a plurality of buttons to which information of different places in the lumen is assigned so as to be distinguishable from each other, and the information correction unit is configured to, by pressing one of the buttons of the input operation device, overwrite the place information regarding the imaging place already associated with the still image with information of a place in the lumen assigned to the pressed button as the place information regarding the imaging place.

Preferably, the still image is an image acquired in each of a plurality of different places in the lumen, and the processor is provided with:

an image evaluation unit configured to calculate an image evaluation value indicating intensity of a lesion of the living tissue in the still image on the basis of a pixel value of the still image;

a spread evaluation unit configured to obtain spread information of the lesion in a depth direction in the lumen by using place information regarding the imaging place associated with the still image in each of a plurality of places in the lumen and the image evaluation value of the still image in each of the plurality of places in the lumen;

and a lumen evaluation unit configured to evaluate severity of the lesion in the lumen on the basis of the image evaluation value in each of the plurality of places in the lumen and the spread information of the lesion.

Advantageous Effects of Invention

According to the electronic endoscope system described above, it is possible to efficiently acquire the information of the imaging place of the still image without providing a dedicated sensor in the electronic endoscope and associate the information with the still image.

BRIEF DESCRIPTION OF DRAWINGS

FIG. 3 is a diagram illustrating an example of processing performed by the electronic endoscope system of one embodiment.

DESCRIPTION OF EMBODIMENTS

Figure 1:
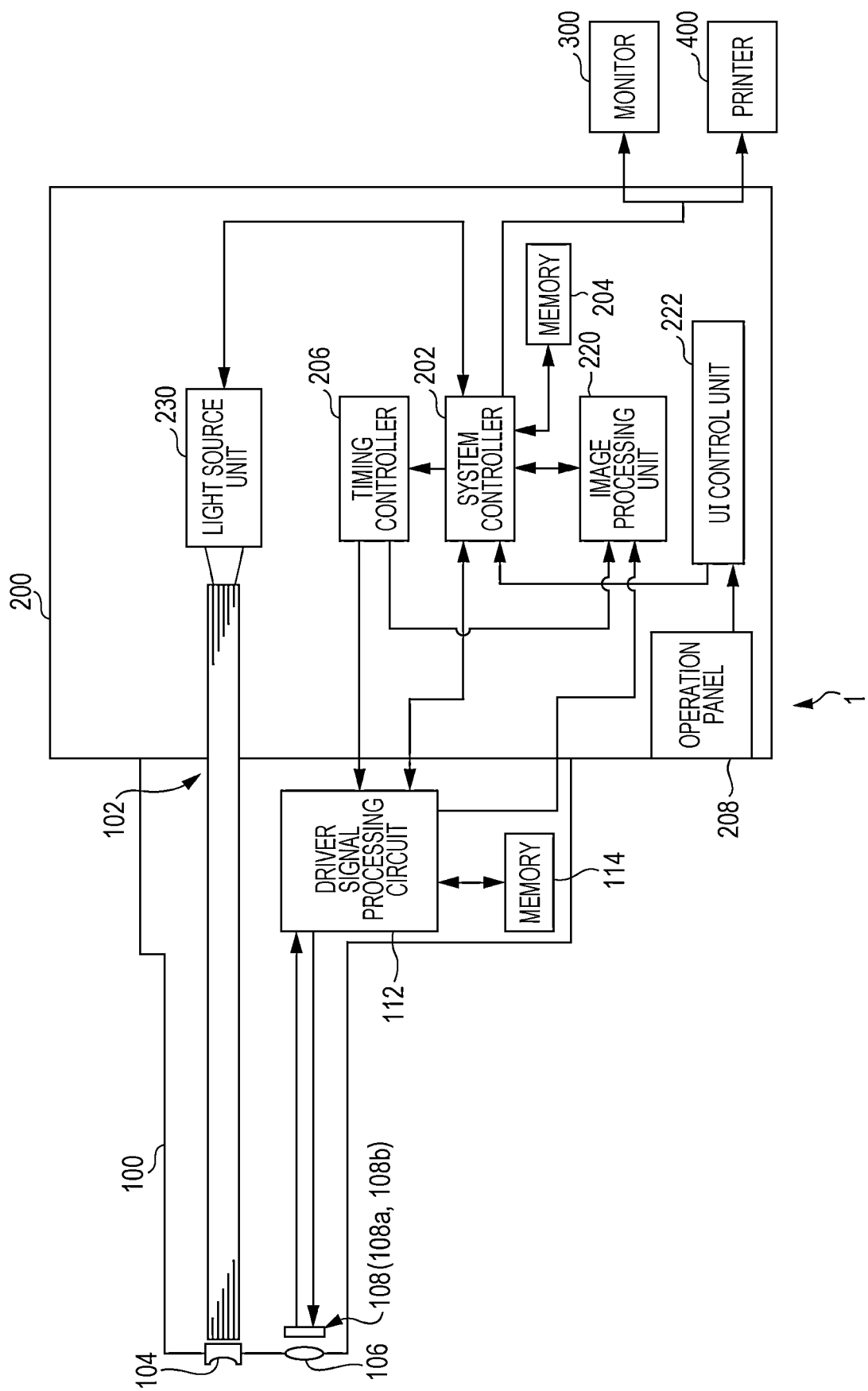
FIG. 1 is a block diagram illustrating a configuration example of an electronic endoscope system of one embodiment.

Hereinafter, an electronic endoscope system of an embodiment is described with reference to the drawings.

(Place Information Regarding Imaging Place of Still Image and Capture Instruction)

A processor of an electronic endoscope system of the embodiment described below acquires a still image from a moving image of living tissue in an organ imaged by an electronic endoscope. This still image is used, for example, for evaluating a lesion degree in a lumen. In a case of imaging the living tissue in the organ as the moving image, for example, the electronic endoscope (hereinafter, referred to as an electronic scope) is inserted from an open end of a tubular organ to a deepest position in the organ in a depth direction to be imaged, and this images the living tissue in the organ while moving from there substantially continuously toward the open end of the organ. The depth direction includes both a direction from the open end toward the deepest position and a direction from the deepest position toward the open end.

The imaged image of the living tissue is displayed on a monitor, and a frame image of the moving image preferred by an operator is acquired as the still image by a capture instruction. Herein, in a case of moving the electronic scope in the lumen, a moving speed of the electronic scope need not necessarily be constant, and it is also possible to return to a place where the electronic scope passes to image, that is, to partially move backward. In one embodiment, in a case of the moving image, the electronic endoscope images while moving in substantially the same direction at substantially the same moving speed.

The acquired still image is preferably associated with place information regarding an imaging place such that an imaging position of the image in the lumen is known.

Therefore, according to the embodiment, a processor of an electronic endoscope system is provided with a still image acquisition unit configured to acquire a part of an imaged moving image of living tissue as a still image by an instruction, an association processing unit configured to associate place information regarding an imaging place of the living tissue in a lumen with the still image, and a recording unit configured to record an acquired still image and the place information regarding the imaging place. An input operation device of the electronic endoscope system performs an operation of determining one place out of a plurality of places in the lumen set in advance as a selected place. The input operation device is configured to transmit a capture instruction to acquire a still image from a moving image to the still image acquisition unit in response to this operation as a trigger, and further transmit, by pressing of one of a plurality of buttons, information of a place in the lumen assigned to the pressed button to the association processing unit as the place information regarding the imaging place during an imaging period of the moving image. As a result, it is possible to issue an instruction to acquire a still image and associate the place information regarding the imaging place with the still image at the same time. Therefore, it is possible to efficiently acquire the information of the imaging place of the still image without providing a dedicated sensor in the electronic endoscope as in the related art and associate this information with the still image.

According to one embodiment, the input operation device is provided with a plurality of buttons to which information of different places in the lumen is assigned so as to be distinguishable from one another. The input operation device is configured to determine a selected place by pressing of one of these buttons, and make the pressing of one of these buttons a trigger for transmission of the capture instruction. According to another embodiment, the input operation device is provided with a selection operation device configured to select a selected place and a determination operation device configured to determine the selected place. The input operation device is configured to transmit the capture instruction to the still image acquisition unit in response to a determination operation by the determination operation device as a trigger.

(Description of Electronic Endoscope System)

FIG. 1 is a block diagram illustrating a configuration example of an electronic endoscope system 1 of one embodiment. As illustrated in FIG. 1, the electronic endoscope system 1 is provided with an electronic scope 100, a processor for an electronic endoscope 200, a monitor 300, and a printer 400.

The processor for an electronic endoscope 200 is provided with a system controller 202 and a timing controller 206. The system controller 202 executes various programs stored in a memory 204, and integrally controls an entire electronic endoscope system 1. The system controller 202 changes various settings of the electronic endoscope system 1 in response to an instruction by a user (operator or assistant) input to an operation panel 208. The timing controller 206 outputs a clock pulse for adjusting an operation timing of each unit to each circuit in the electronic endoscope system 1.

The processor for an electronic endoscope 200 is provided with a light source unit 230 that supplies illumination light to the electronic scope 100. Although not illustrated, the light source unit 230 is provided with, for example, a high-luminance lamp that is supplied with drive power from a lamp power source to emit white illumination light such as a xenon lamp, a metal halide lamp, a mercury lamp, or a halogen lamp, for example. The light source unit 230 is configured such that the illumination light emitted from the high-luminance lamp is condensed by a condensing lens not illustrated and then incident on an incident end of a light carrying bundle (LCB) 102 of the electronic scope 100 via a dimmer not illustrated.

Alternatively, the light source unit 230 is provided with a plurality of light emitting diodes for emitting a light beam of a wavelength band of a predetermined color. The light source unit 230 is configured such that the light beams emitted from the light emitting diodes are synthesized by using an optical element such as a dichroic mirror, and the synthesized light is condensed by a condensing lens not illustrated as the illumination light and then incident on the incident end of the light carrying bundle (LCB) 102 of the electronic scope 100. A laser diode may be used in place of the light emitting diode. Since the light emitting diode and the laser diode have characteristics such as low power consumption and a low heat generation amount as compared with other light sources, there is an advantage that a bright image may be acquired while suppressing the power consumption and the heat generation amount. Since the bright image may be acquired, accuracy in image evaluation value may be improved.

Note that, although the light source unit 230 is incorporated in the processor for an electronic endoscope 200 in the example illustrated in FIG. 1, this may also be provided in the electronic endoscope system 1 as a device separate from the processor for an electronic endoscope 200. The light source unit 230 may also be provided in a distal tip of the electronic scope 100 to be described later. In this case, the LCB 102 that guides the illumination light is not necessary.

The illumination light incident on the incident end to enter the LCB 102 propagates through the LCB 102 to be emitted from an end of the LCB 102 arranged in the distal tip of the electronic scope 100, and is applied to living tissue in an organ, which is an object, via a light distribution lens 104. Reflected light from the living tissue forms an optical image on a light receiving surface of an image sensor 108 via an objective lens 106.

The image sensor 108 is, for example, a single-plate type color charge-coupled device (CCD) image sensor in which various filters such as an infrared (IR) cut filter 108a and a Bayer pattern color filter 108b are arranged on the light receiving surface, and generates primary color signals of red (R), green (G), and blue (B) according to the optical image formed on the light receiving surface. In place of the single-plate type color CCD image sensor, a single-plate type color complementary metal oxide semiconductor (CMOS) image sensor may also be used. An image tends to be darker as a whole with the CMOS image sensor than with the CCD image sensor in general. Therefore, an advantageous effect of suppressing fluctuation in severity of a lesion in a lesion area due to brightness of the image in quantification processing of evaluating the lesion degree described below is more remarkable in a case of using the CMOS image sensor. In this manner, the electronic scope 100 uses the image sensor 108 to image the living tissue in the organ and generate a moving image.

A driver signal processing circuit 112 is provided in a connection portion to the processor 200 of the electronic scope 100. The driver signal processing circuit 112 generates image signals (luminance signal Y and color difference signals Cb and Cr) by performing predetermined signal processing such as color interpolation and a matrix operation on the primary color signals input from the image sensor 108, and outputs the generated image signals to an image processing unit 220 of the processor for an electronic endoscope 200. The driver signal processing circuit 112 also accesses a memory 114 and reads specific information of the electronic scope 100. The specific information of the electronic scope 100 recorded in the memory 114 includes, for example, the number of pixels and sensitivity of the image sensor 108, an operable frame rate, a model number and the like. The driver signal processing circuit 112 outputs the specific information read from the memory 114 to the system controller 202.

The system controller 202 performs various arithmetic operations on the basis of information stored in the memory 204 and the specific information of the electronic scope 100, and generates a control signal. The system controller 202 controls an operation and a timing of each circuit in the processor for an electronic endoscope 200 by using the generated control signal so that processing suitable for the electronic scope 100 currently connected to the processor for an electronic endoscope 200 is performed.

The timing controller 206 supplies the clock pulse to the driver signal processing circuit 112, the image processing unit 220, and the light source unit 230 in accordance with timing control by the system controller 202. The driver signal processing circuit 112 performs drive control of the image sensor 108 at a timing synchronized with a frame rate of a video processed on a side of the processor for an electronic endoscope 200 in accordance with the clock pulse supplied from the timing controller 206.

Figure 2:
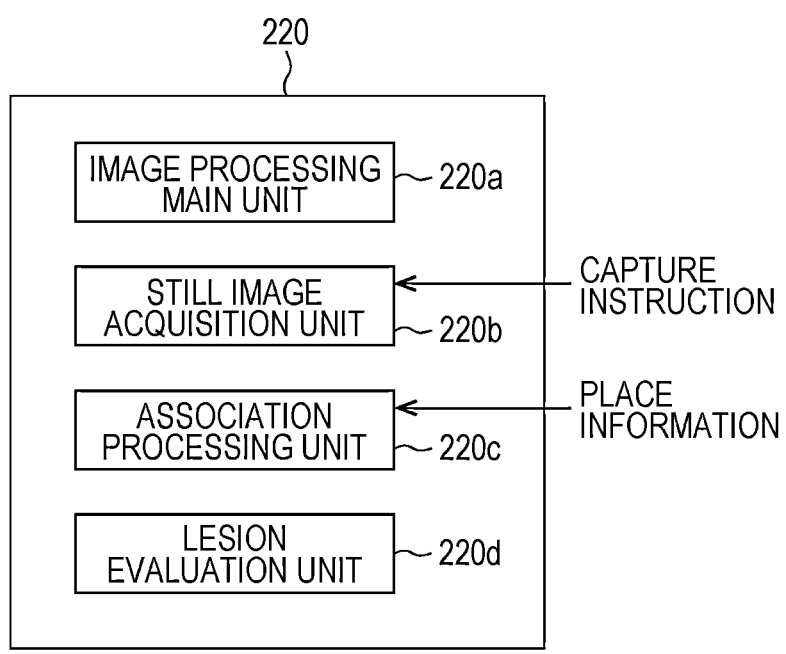
FIG. 2 is a diagram illustrating a configuration example of an image processing unit of the electronic endoscope system of one embodiment.

FIG. 2 is a diagram illustrating a configuration example of the image processing unit of the electronic endoscope system 1 of one embodiment.

The image processing unit 220 is provided with an image processing main unit 220a, a still image acquisition unit 220b, an association processing unit 220c, and a lesion evaluation unit 220d.

The image processing main unit 220a performs processing set in advance on the image signal transmitted from the driver signal processing circuit 112, and generates a moving image signal for reproducing an image as a moving image on a monitor 300. In addition to displaying the moving image on a screen, in a case of acquiring a one-frame image of the moving image as a still image, the monitor 300 also displays the still image.

The still image acquisition unit 220b acquires the one-frame image of the moving image displayed on the monitor 300 as the still image by a capture instruction from the operation panel 208, which is a touch panel to be described later. The acquired still image is recorded and held in the memory 204.

When the still image acquisition unit 220b acquires the still image, the association processing unit 220c associates the still image with place information regarding an imaged place transmitted from the operation panel 208. As for the association, an association method is not limited as long as the place information regarding the imaging place may be specified for the still image. For example, the association may be such that order of acquisition of the still image and order of selection of the place information correspond to each other, or such that a time when the still image is acquired and a time when the place information is set may correspond to each other.

The lesion evaluation unit 220d evaluates the lesion by using the acquired still image.

For example, since an inflammation portion in ulcerative colitis has a thinner mucosa than that in a normal portion and exhibits redness, a degree of redness (hereinafter, simply referred to as a redness degree) may be quantified by using a ratio of a pixel value of a red component of each pixel of the still image to a pixel value of another color component, for example, a G component when the white light is used as the illumination light. The redness degree may represent a degree of inflammation in a minute region corresponding to each pixel. It is possible to evaluate intensity of the lesion (representing progress of the lesion) in the still image by using an integrated value obtained by integrating such redness degree for each pixel over an entire still image, an average value or the like. The intensity of the lesion using such redness degree is specifically disclosed in, for example, WO 2017/057680 A. Specifically, in a color plane defined by at least two color components out of a color image including at least three or more color components, it is evaluated regarding the intensity of the lesion of each pixel on the basis of an angle formed by a line segment connecting a predetermined reference point set in the color plane and a pixel corresponding point in the color plane of each pixel forming the acquired color image and a reference axis having correlation with the lesion.

Since the still image to be evaluated is associated with the place information regarding the imaging place by association by the association processing unit 220c, the lesion evaluation unit 220d may know distribution of the intensity of the lesion in the depth direction in the lumen by using the intensity of the lesion for each of a plurality of still images, and may know spread of the lesion in the depth direction in the lumen.

The still image acquired by the still image acquisition unit 220b is acquired as the one-frame image of the moving image by the user pressing a button displayed on the operation panel 208 while viewing the moving image displayed on the monitor 300. At that time, the operation panel 208 displays a plurality of buttons to which information of different places in the lumen is assigned so as to be distinguishable from each other. By pressing one of these buttons, the information of the place in the lumen assigned to the pressed button is selected as the place information regarding the imaging place, and the place information is transmitted to the association processing unit 220c.

That is, the operation panel 208 is an input operation device that performs an operation of determining one place out of a plurality of places in the lumen set in advance as a selected place, transmits the capture instruction for acquiring the still image from the moving image to the still image acquisition unit 220b in response to this operation as a trigger, and further transmits information of the selected place to the association processing unit 220c as the place information regarding the imaging place during an imaging period of the moving image.

The button, which is the input operation device, performs operations of the capture instruction and the selection and determination of the place information regarding the imaging place, and the operations are controlled by a user interface (UI) control unit 222 provided in the processor 200. That is, the UI control unit 222 allows the operation panel 208 to display the plurality of buttons, controls such that the user selects and presses one of the plurality of buttons to determine the selected place, and further generates a control signal of the capture instruction and a control signal of the place information regarding the imaging place. In this case, the control signal of the place information regarding the imaging place includes information of the place (selected place) assigned to the pressed button on the operation panel 208. These control signals are transmitted to the image processing unit 220 via the system controller 202.

FIG. 3 is a diagram illustrating an example of processing performed by the electronic endoscope system of one embodiment in a case of inspecting the inside of the large intestine. On the operation panel 208, "rectum capture", "sigmoid capture" and the like are displayed on the buttons. That is, the information of different places in the lumen is assigned to the buttons so as to be distinguishable from each other.

A still image capture instruction is transmitted to the still image acquisition unit 220b in response to an operation of pressing one of the buttons as a trigger, so that the still image is acquired from the moving image. Furthermore, the selected place is determined by selecting and pressing the button on which "rectum capture", "sigmoid capture" or the like is displayed, and the information of the selected place, for example, the place information such as "rectum" and "sigmoid" is transmitted to the association processing unit 220c. The association processing unit 220c associates the acquired still image with the place information such as "rectum" and "sigmoid". The acquired still image and the place information are recorded and held in the memory 204.

Figure 4A:
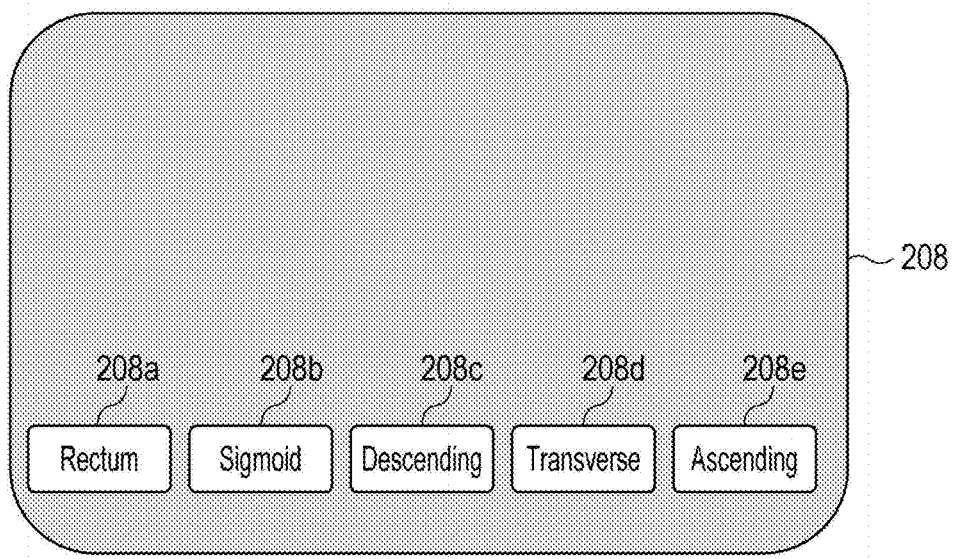
FIGS. 4(a) to 4(c) are views illustrating examples of buttons displayed on an operation panel of the electronic endoscope system of one embodiment.
Figure 4B:
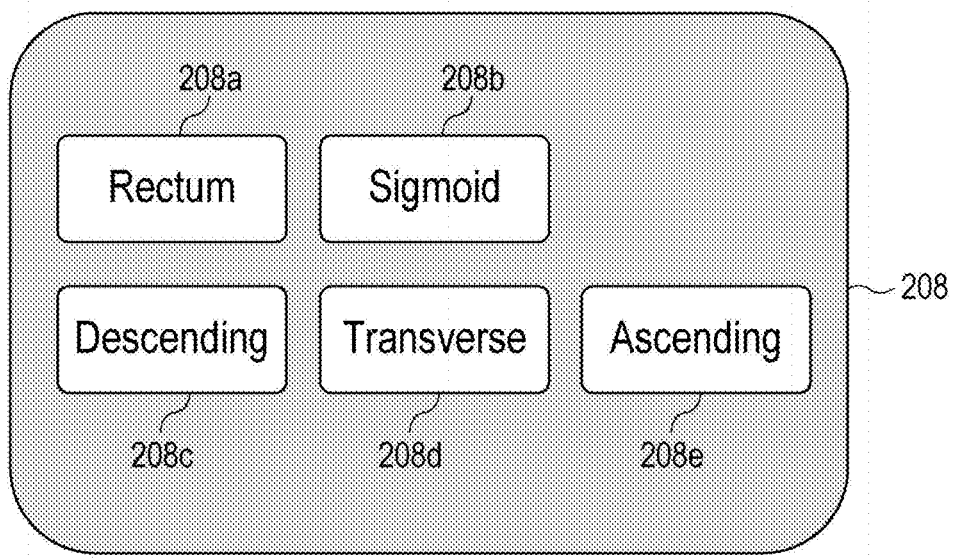
Figure 4C:
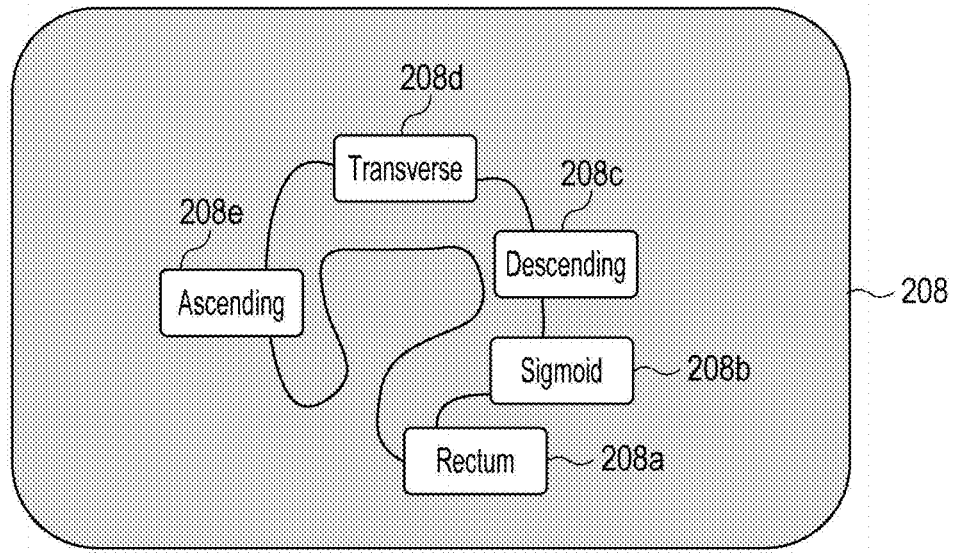

FIGS. 4(a) to 4(c) are views illustrating examples of the buttons displayed on the operation panel 208. On buttons 208a to 208e illustrated in FIGS. 4(a) to 4(c), names of different places of the large intestine are displayed, and they may be distinguished from each other. "Rectum" (rectum) is displayed on the button 208a, "Sigmoid" (sigmoid) is displayed on the button 208b, "Descending" (descending colon) is displayed on the button 208c, "Transverse" (transverse colon) is displayed on the button 208d, and "Ascending" (ascending colon) is displayed on the button 208e, and by pressing one of the buttons 208a to 208e, a display content corresponding to the pressed button is determined as selected place information, and the selected place information is transmitted to the association processing unit 220c as the place information regarding the imaging place.

The buttons 208a to 208e may be arranged to form a row in a lateral direction as illustrated in FIG. 4(a), arranged in a plurality of stages as illustrated in FIG. 4(b), and it is also possible to display a shape of the large intestine and arrange the buttons on which the names corresponding to respective places of the shape are displayed as illustrated in FIG. 4(c).

The buttons 208a to 208e illustrated in FIGS. 4(a) to 4(c) are examples in which the names of the places in the lumen are assigned; in addition to this, distance information from the open end of the lumen may be assigned to the buttons 208a to 208e. For example, the distance information such as "to 10 cm", "to 20 cm", and "to 30 cm" may be assigned to the buttons 208a to 208e as the selected place information. As for such distance information, since the user (operator or assistant) manually inserts a flexible tube of the electronic scope 100 into the lumen and then inspects the inside of the lumen while pulling out the same, the user roughly grasps the distance information from the open end regarding the place to be imaged by the image sensor 108 in the distal tip of the electronic scope 100, so that there is no inconvenience for the user even when the distance information such as "to 10 cm", "to 20 cm", and "to 30 cm" is assigned to the buttons 208a to 208e as the information of the selected place.

It is also possible to allocate a number (identification information) to each place in the depth direction in the lumen, and assign this number (identification information) to the buttons 208a to 208e as the information of the selected place in place of the distance information from the open end. Since the user grasps in advance a place in the depth direction in the lumen allocated with such number (identification information) as the information of the selected place, and the user manually inserts the flexible tube of the electronic scope 100 into the lumen and then inspects the inside of the lumen while pulling out the same, the user grasps the place imaged by the image sensor 108 in the distal tip of the electronic scope 100, so that there is no inconvenience for the user even with the buttons 208a to 208e to which the number (identification information) is assigned.

In this manner, since the name of the place in the lumen, the distance from the open end of the lumen, or the identification information specifying the place of the lumen is set as the information of the selected place in the lumen, the user may select an appropriate button out of the buttons 208a to 208e, issue the capture instruction of the still image, and further associate the acquired still image with correct place information.

Note that, in the examples illustrated in FIGS. 4(a) to 4(c), there are five divided places in the lumen, but the number thereof is not limited to five. There may be six or more divided places, or may be seven, nine, or 15 divided places.

In this manner, since the button is such that the name of the place in the lumen, the distance information from the open end of the lumen, or the identification information is displayed on the touch panel as the information of the selected place in the lumen, the user may simultaneously transmit the capture instruction and the place information regarding the selected and determined imaging place to the image processing unit 220 in response to an operation of pressing a desired button as a trigger. Therefore, this is excellent in user friendliness.

Figure 5:
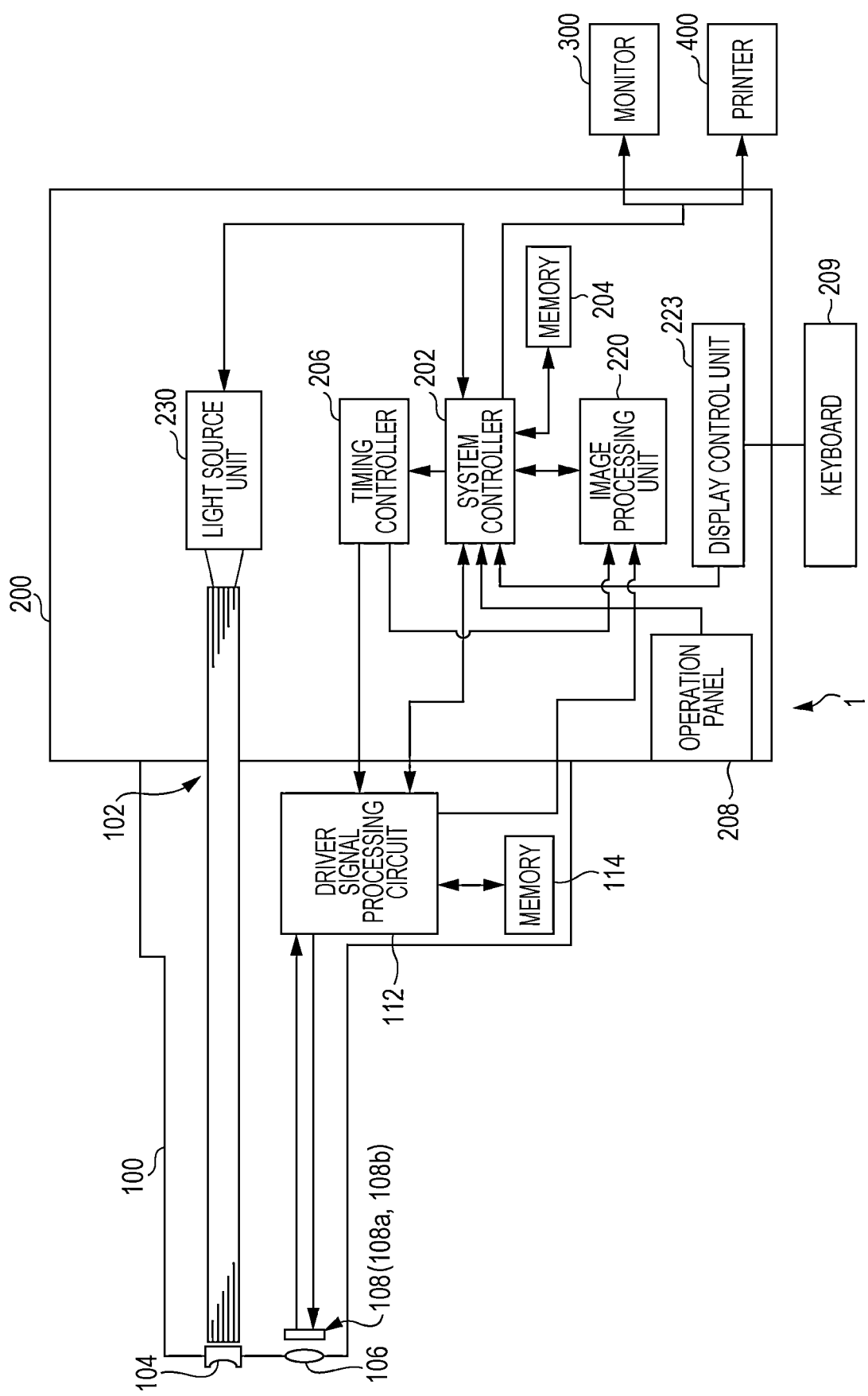
FIG. 5 is a diagram illustrating a configuration example different from that in FIG. 1 of the electronic endoscope system of one embodiment.

In the example of the electronic endoscope system 1 illustrated in FIG. 1, the operation panel 208 is used as the input operation device, and the capture instruction and the place information regarding the imaging place are transmitted to the image processing unit 220 by the pressing of the button displayed on the operation panel 208; the input operation device may be a keyboard, and the button may be a key of the keyboard. FIG. 5 is a diagram illustrating a configuration example different from the configuration illustrated in FIG. 1 of the electronic endoscope system 1 of one embodiment. Since the electronic scope 100, the monitor 300, and the printer 400 illustrated in FIG. 5 are the same as the electronic scope 100, the monitor 300, and the printer 400 illustrated in FIG. 1, the description of these devices is omitted.

The processor for an electronic endoscope 200 illustrated in FIG. 5 is provided with a display control unit 223 connected to a keyboard 209 in place of the UI control unit 222 of the processor for an electronic endoscope 200 illustrated in FIG. 1. The configuration other than this is the same as the configuration of the processor 200 illustrated in FIG. 1, so that the description thereof is omitted.

The display control unit 223 allocates functions to be described below to the respective keys of the keyboard 209, and controls via the system controller 202 to display a key allocation content on the monitor 300.

Specifically, the display control unit 223 controls to display information in which the information of the place in the lumen set as the information of the selected place in the key of the keyboard 209 is associated with the number, character, or symbol set in the key on the monitor 300. By selecting and pressing one of the keys, the capture instruction allocated to the key is transmitted to the image processing unit 220 in response to this pressing as a trigger, and furthermore, the information of the selected place determined by the pressing is transmitted to the image processing unit 220 as the place information regarding the imaging place.

Figure 6A:
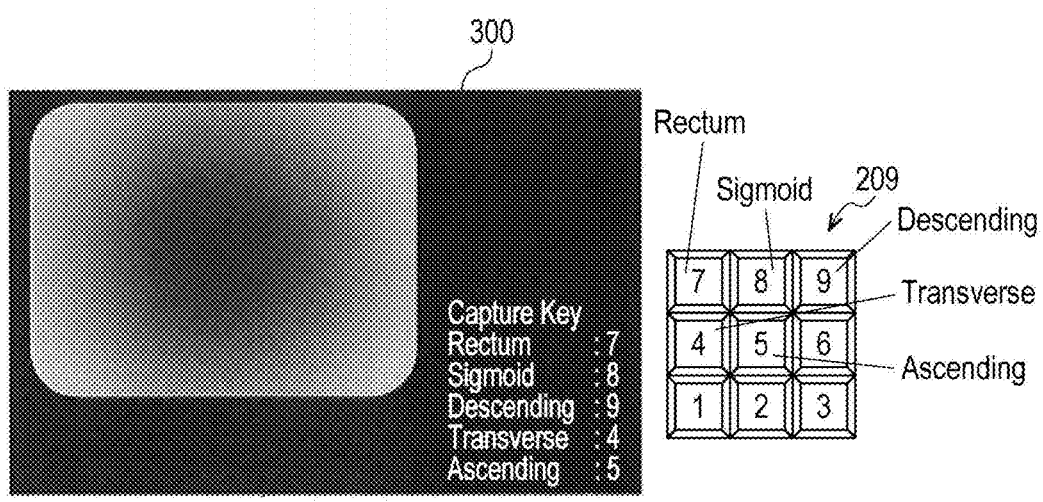
FIGS. 6(a) and 6(b) are views illustrating a key allocation content of a keyboard, and an example of display of the key allocation content displayed on a monitor of the electronic endoscope system of one embodiment.
Figure 6B:
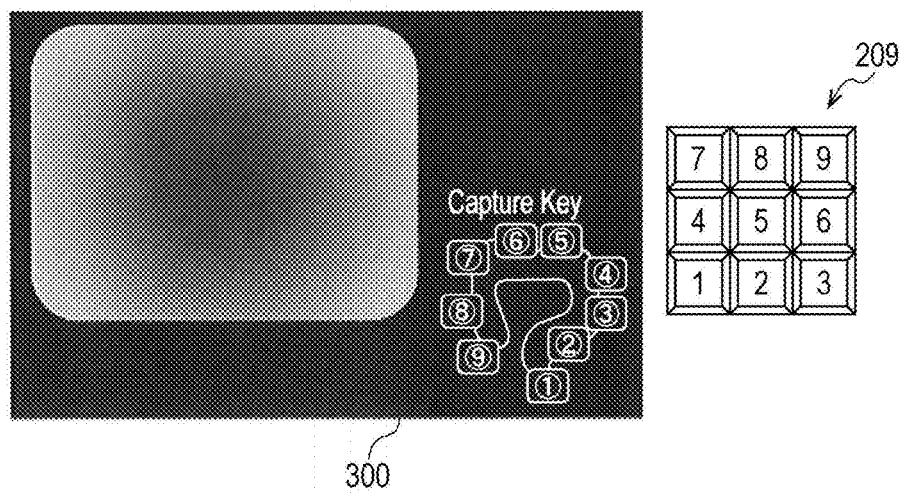

FIGS. 6(a) and 6(b) are views illustrating the key allocation content of the keyboard 209, and an example of display of the key allocation content displayed on the monitor 300.

In the example illustrated in FIG. 6(a), on the screen of the monitor 300, a current moving image, and the number of the key and the information of the selected place for the capture instruction are displayed. FIG. 6(a) illustrates that a key number "7" is allocated to the capture instruction in the imaging place of "Rectum" (rectum), a key number "8" is allocated to the capture instruction in the imaging place of "Sigmoid" (sigmoid), a key number "9" is allocated to the capture instruction in the imaging place of "Descending" (descending colon), a key number "4" is allocated to the capture instruction in the imaging place of "Transverse" (transverse colon), and a key number "5" is allocated to the capture instruction in the imaging place of "Ascending"

(ascending colon). Therefore, for example, by pressing the key number "7", the rectum is determined as the selected place in response to this pressing as a trigger, and furthermore, the capture instruction of the still image is generated.

In the example illustrated in FIG. 6(b), the current moving image and information indicating each place of the large intestine by "①"~"⑨"

is displayed on the screen of the monitor 300. It is illustrated that "①"~"⑨"

are allocated corresponding to the key numbers "1" to "9" of the keyboard 209. Therefore, for example, by pressing the key of the number "1", the place of "①"

of the large intestine is determined as the selected place in response to the pressing as a trigger, the information and the capture instruction are generated, and the information of the selected place and the capture instruction are transmitted to the image processing unit 220.

In this manner, since the allocation content to the respective keys of the keyboard 209 is displayed together with the display of the moving image on the monitor 300, the user may simultaneously transmit the capture instruction and the place information regarding the imaging place to the image processing unit 220 by pressing a desired key while viewing the monitor 300. Therefore, this is excellent in user friendliness.

The input operation device used in the above-described embodiment is provided with a plurality of buttons to which the information of different places in the lumen is assigned so as to be distinguishable from each other, determines the selected place in response to the pressing of one of the plurality of buttons as a trigger, and further makes the pressing of one of the above-described buttons a trigger for transmission of the capture instruction; however, it is possible to use a slider, a wheel and the like displayed on the operation panel 208 or the monitor 300 in place of the plurality of buttons, select information of a place displayed on the slider and the wheel (select the selected place) by an input operation on the touch panel and an input operation from a mouse and the like, and determine the selected place. The selected place is determined, for example, in a case where the input operation to the slider, the wheel and the like is not performed for a certain period of time. These input operations is substantially controlled by the UI control unit 222 or the display control unit 223.

In a case where the operation panel 208 is the touch panel, the touch panel may be configured to be able to select a content of an operation by detecting a direction in which a user's finger moves on the operation panel 208 as a flick input used in a smartphone, and configured to make information of a place corresponding to the detected direction the information of the selected place (select the selected place) by detecting the direction in which the finger moves on the touch panel, thereby determining the selected place. The selected place is determined, for example, in a case where the direction in which the user's finger moves is not detected for a certain period of time. These operations are substantially controlled by the UI control unit 222 or the display control unit 223.

In the above-described embodiment, the selection and determination of the selected place is performed by one operation, but in another embodiment, the selection and determination of the selected place may be performed by separate operations. In this case, the input operation device may be provided with a selection operation device configured to select one selected place out of a plurality of places and a determination operation device configured to determine the selected place. In this case, it is preferable to configure such that the information of the determined selected place is transmitted to the association processing unit 220c and the capture instruction is transmitted to the still image acquisition unit 220b in response to the determination operation by the determination operation device as a trigger.

Examples of the above-described determination operation device may include a user interface including an operation button provided on an operation unit of the electronic scope 100 or a single switch such as a foot switch not illustrated connected to the processor 200, for example. In this case, as the above-described selection operation device that selects the selected place, for example, the user interface that selects one selected place by switching the place information with a toggle switch or a toggle button may be used.

As the user interface that selects the selected place, a mode of using the user interface such as the above-described slider, wheel and the like displayed on the operation panel 208 or the monitor 300, or a mode of using the user interface capable of selecting the operation content by detecting the direction in which the user's finger moves on the operation panel 208 as the flick input used in a smartphone may be used. It goes without saying that, the plurality of buttons described above may also be used as the selection operation device. In this case, by selecting and pressing one of the buttons, the place corresponding to the button may be selected as the selected place. It is not limited to the plurality of buttons, and it is also possible that the information of the place is switched each time one button is pressed, and the pressing may be repeated until the information is switched to the information of a target selected place. It is also possible to configure the selection operation device such that the information of the place at the time of pressing is selected as the information of the selected place by keeping pressing the button for several seconds. In this case, the information of the place switched by the pressing of the button is displayed on the monitor 300.

Note that, according to one embodiment, the association processing unit 220c preferably writes the place information regarding the imaging place in the still image acquired by the capture instruction. This makes it possible to reliably associate the still image with the place information.

Figure 7:
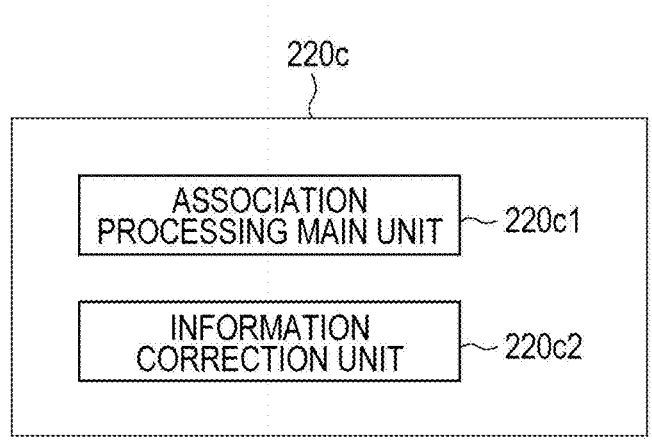
FIG. 7 is a diagram illustrating an example of a configuration of an association processing unit of the electronic endoscope system of one embodiment.

According to one embodiment, as illustrated in FIG. 7, the association processing unit 220c of the processor 200 is preferably provided with an association processing main unit 220c1 that performs association processing between the still image and the place information regarding the imaging place at the time of acquisition of the still image described above, and an information correction unit 220c2. The information correction unit 220c2 has a function of overwriting the place information regarding the imaging place already associated with the still image with one place selected from a plurality of places in the lumen set in advance as the place information regarding the imaging place outside an imaging period of the moving image for the still image to which the place information regarding the imaging place is associated as erroneous information. According to one embodiment, there is a function of overwriting the place information regarding the imaging place already associated with the still image with the information of the place in the lumen assigned to the pressed button as the place information regarding the imaging place by the pressing of one of the buttons of the input operation device such as the operation panel 208 or the keyboard 209. FIG. 7 is a diagram illustrating an example of a configuration of the association processing unit 220c of the processor 200 of one embodiment.

Figure 8:
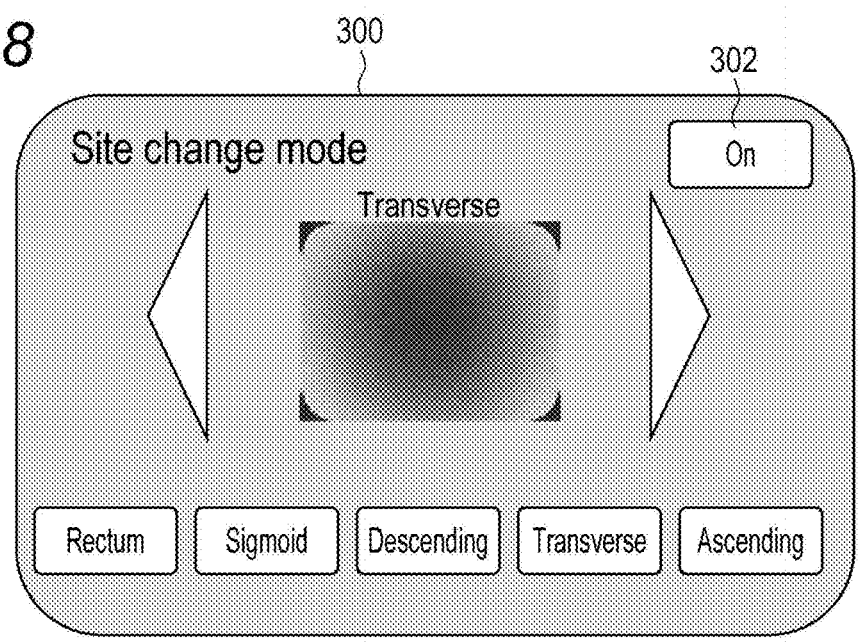
FIG. 8 is a diagram illustrating an example of a display screen of the monitor when an information correction unit of the electronic endoscope system of one embodiment is allowed to function.

FIG. 8 is a diagram illustrating an example of a display screen of the monitor 300 when the information correction unit 220c2 of the processor for an electronic endoscope 200 of one embodiment is allowed to function. The example illustrated in FIG. 8 illustrates that the still image is displayed on the monitor 300, and the place information associated with the still image is "Transverse" (transverse colon) erroneously set. In this case, by clicking an "On" button 302, it enters a correction mode of the place information. In this correction mode, by clicking buttons such as "Rectum" and "Sigmoid" arranged on a lower side of the still image, "Transverse" is overwritten with correct place information. In this case, the place information corresponding to the acquired still image is overwritten to be changed. The information correction unit 220c2 controls the monitor 300 such that an immediately preceding still image or an immediately following still image of the acquired still image is displayed on the screen of the monitor 300 by clicking triangular arrows provided on both sides of the still image on the display screen.

Figure 9:
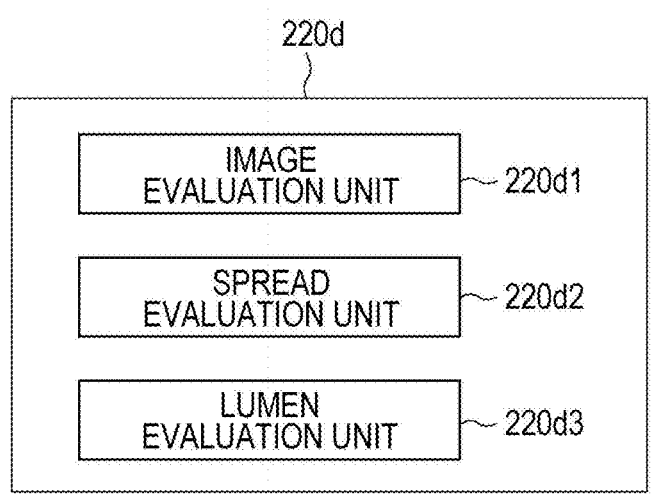
FIG. 9 is a diagram illustrating an example of a configuration of a lesion evaluation unit of the electronic endoscope system of one embodiment.

According to one embodiment, the lesion evaluation unit 220d (refer to FIG. 2) of the processor 200 is provided with an image evaluation unit 220d1, a spread evaluation unit 220d2, and a lumen evaluation unit 220d3 as illustrated in FIG. 9. FIG. 9 is a diagram illustrating an example of a configuration of the lesion evaluation unit 220d of the processor 200 of one embodiment.

The image evaluation unit 220d1 is configured to calculate an image evaluation value indicating the intensity of the lesion of the living tissue in the still image on the basis of the pixel value of the still image. The still image evaluated by the image evaluation unit 220d1 is the image acquired in each of a plurality of different places in the lumen.

The spread evaluation unit 220d2 is configured to obtain spread information of the lesion in the depth direction in the lumen by using the place information regarding the imaging place associated with the still image in each of the plurality of places in the lumen and the image evaluation value of the still image in each of the plurality of places in the lumen.

The lumen evaluation unit 220d3 is configured to evaluate the severity of the lesion in the lumen on the basis of the image evaluation value in each of the plurality of places in the lumen and the spread information of the lesion.

The image evaluation unit 220d1 first makes the redness degree of the living tissue obtained by quantifying the degree of redness of the living tissue in the still image for each pixel the pixel evaluation value, and calculates a value obtained by putting the pixel evaluation values of the respective pixels of the image together to one numerical value by integration processing or averaging processing, for example, as the image evaluation value. That is, the degree of inflammation of the living tissue is evaluated by using the degree of redness of the living tissue. Hereinafter, a mode of calculating the living tissue redness degree indicating the intensity of inflammation is described as an example.

In preprocessing before calculating the living tissue redness degree, each processing of RGB conversion, color conversion, reference axis setting, and color correction is performed.

The image processing unit 220 to which the luminance signal Y and the color difference signals Cb and Cr are input from the driver signal processing circuit 112 converts the same into image color components (R, G, B) using a predetermined matrix coefficient. This further performs the color conversion of normally projecting image data converted into the image color components onto an RG plane as the preprocessing. Specifically, the image color component of each pixel in an RGB color space defined by three primary colors of RGB is converted into the image color component of RG. Conceptually, the image color component of each pixel in the RGB color space is plotted in the RG plane (for example, a partition in the RG plane taking a pixel value of an R component=0 to 255 and a pixel value of a G component=0 to 255) according to the pixel values of the R and G components. Hereinafter, for convenience of description, a point of the image color component of each pixel in the RGB color space and a point of the image color component plotted in the RG color space are referred to as a "pixel corresponding point". The image color components of RGB in the RGB color space are, for example, the color components of wavelengths of 620 to 750 nm, 495 to 570 nm, and 450 to 495 nm, respectively, in this order. Note that the color components form the color space (including the color plane). Hue and saturation are excluded from the "color components".

Furthermore, the image evaluation unit 220d1 sets the reference axis in the RG plane necessary for evaluating the living tissue redness degree. In the RG color plane, a straight line passing through (50,0) and (255,76) is set as one of the reference axes, for example, and a straight line passing through (0,0) and (255,192) is set as one of the reference axes, for example. The former reference axis is a "hemoglobin change axis", and the latter reference axis is a "mucosa change axis". The pixel values of the R component and the G component on the "hemoglobin change axis" have values of the R component and the G component of hemoglobin regardless of intensity of the illumination light, the axis indicating a state in which the inflammation progresses most to exhibit redness. In contrast, the pixel values of the R component and the G component on the "mucosa change axis" have the values of the R component and the G component of the normal portion covered with the mucosa regardless of the intensity of the illumination light, the axis indicating a state in which there is no inflammation. Therefore, it is possible to plot the values of the R component and the G component of each pixel of the still image in the RG plane and quantify the intensity of the lesion in each pixel by a slip angle from the "hemoglobin change axis" or the "mucosa change axis" of a straight line connecting the plotted point and an intersection of the above-described two reference axes. For example, by assuming that the angle between the "hemoglobin change axis" and the "mucosa change axis" is 100, and quantifying the slip angle between the straight line connecting the plotted point and the above-described intersection and the "mucosa change axis" with a value of 0 to 100, the intensity of the lesion in each pixel may be indicated. This numerical value is referred to as the pixel evaluation value of each pixel.

The image evaluation unit 220d1 calculates one image evaluation value from the pixel evaluation value of each pixel. The image evaluation unit 220d1 may calculate, for example, the integrated value or the average value of the pixel evaluation values of all the pixels in the still image as one image evaluation value, or may select the pixels representing the image of the living tissue to be evaluated in the still image and calculate the integrated value or the average value of the pixel evaluation values of the selected pixels as one image evaluation value. Alternatively, for example, the image evaluation unit 220d1 may calculate one image evaluation value by extracting the pixels to be evaluated on the basis of, out of the RGB color component or pixel luminance component for each pixel, the color components or luminance components in a predetermined range, and obtaining the average value of the pixel evaluation values of the extracted pixels, or obtaining a weighed average value using a predetermined weighting coefficient, or performing integration processing.

The image evaluation value obtained in this manner is the intensity of the lesion indicating the progress of the lesion of the living tissue in the still image.

As described above, since the still image is associated with the place information regarding the imaging place, it is possible to grasp the intensity of the lesion for the place information regarding the imaging place via the still image. That is, the spread evaluation unit 220d2 may acquire the distribution of the intensity of the lesion in the depth direction in the lumen. For example, the spread evaluation unit 220d2 may acquire the spread information of the lesion by making a graph by plotting the place in the depth direction from the open end in the lumen along the abscissa and plotting the intensity of the lesion in the still image along the ordinate. For example, in a case where the intensity of the lesion is equal to or greater than a predetermined threshold, it is determined that there is the lesion area. As a result, the spread evaluation unit 220d2 may acquire presence or absence of the lesion and the spread information in the depth direction of the lesion.

The lumen evaluation unit 220d3 evaluates the severity of the lesion in the lumen on the basis of the above-described intensity of the lesion and the above-described spread information of the lesion. By using a length of the lesion as a value of the spread information and using the image evaluation value for the intensity of the lesion, or by using, in a case where a plurality of still images is acquired in substantially the same place and there is a plurality of image evaluation values, a representative value thereof, the severity of the lesion in the lumen may be comprehensively evaluated. For example, the lumen evaluation unit 220d3 may classify combinations of the intensity of the lesion and the length of the lesion into a plurality of levels, and evaluate the severity of the lesion by a level according to the level at which the target portion in the lumen to be evaluated is positioned out of the classified levels.

Regarding a still image group of lesion samples, the lumen evaluation unit 220d3 may predict the degree of the lesion of the living tissue in the lumen to be evaluated by an evaluation level by using a prediction model obtained by machine learning of a relationship between the intensity of the lesion and the length of the lesion and the evaluation level using the evaluation level evaluated by a doctor as the Mayo score and data of the combination of the intensity of the lesion and the length of the lesion obtained from the still image as learning data, and may make this evaluation level the severity of the lesion.

In this manner, the lumen evaluation unit 220d3 may accurately evaluate the severity of the lesion in consideration of not only the intensity of the lesion but also the spread of the lesion.

Figure 10:
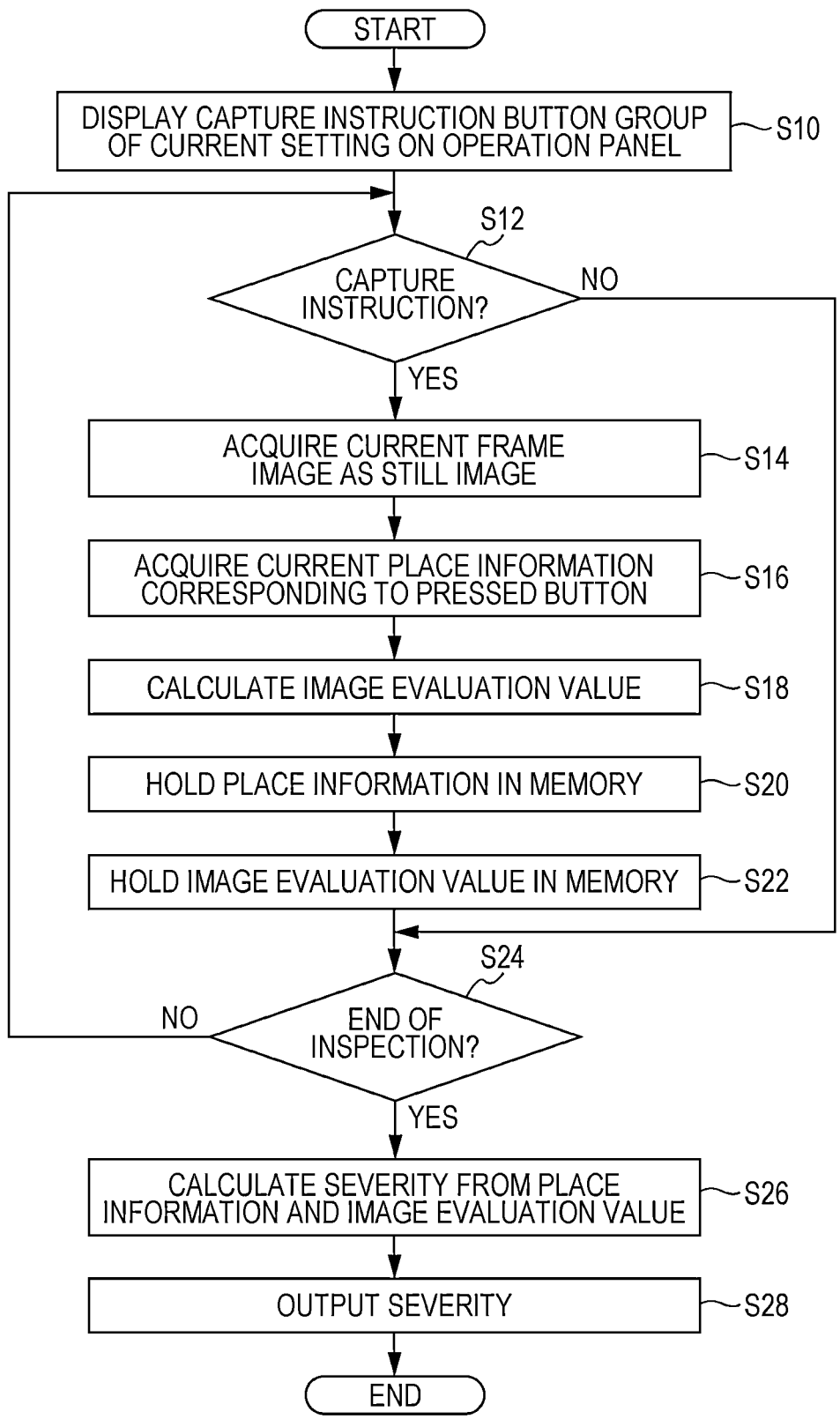
FIG. 10 is a diagram illustrating an example of a flow of acquisition of place information regarding an imaging place performed by using the electronic endoscope system of one embodiment and calculation of severity performed accordingly.

FIG. 10 is a diagram illustrating an example of a flow of acquisition of the place information regarding the imaging place performed by using the electronic endoscope system of one embodiment and calculation of the severity performed accordingly.

First, the electronic endoscope system 1 is started, and the user (operator or assistant) sets a mode of observing and inspecting the living tissue in the lumen. As a result, as illustrated in FIGS. 4(*a*) to 4(*c*), a set button group for capture instruction is displayed on the operation panel 208 under the control of the UI control unit 222 (step S10).

While viewing the image of the living tissue in the lumen imaged by the electronic scope 100 and displayed on the monitor 300, the user selects and presses the button to which the place information regarding the imaging place corresponding to the displayed image is assigned.

The UI control unit 222 determines whether the capture instruction of the image is issued by the pressing of the button (step S12), and in a case where the capture instruction is issued, this creates the control signal of the capture instruction for acquiring the image of a current frame of the moving image displayed on the monitor 300, and transmits the same to the image processing unit 220. As a result, the still image acquisition unit 220b of the image processing unit 220 receives the capture instruction and acquires the still image from the moving image of the current frame displayed on the monitor 300 (step S14).

Furthermore, the association processing unit 220c of the image processing unit 220 receives the place information regarding the imaging place from the UI control unit 222 and acquires the place information (step S16).

Thereafter, the lesion evaluation unit 220d calculates the pixel evaluation value indicating the intensity of the lesion of each pixel from the still image acquired by the still image acquisition unit 220b, and calculates the image evaluation value indicating the intensity of the lesion of the living tissue in the still image (step S18).

At the same time, the association processing unit 220c records to hold the place information in the memory 204 and records to hold the image evaluation value in the memory 204 (steps S20 and S22). In a case where the place information is recorded to be held in the memory 204, the place information is recorded to be held in association with not only the still image but also the image evaluation value.

Next, in a case where the capture instruction of the image is not issued, the system controller 202 determines whether the inspection of the living tissue in the lumen ends (step S24). There is an inspection end button on the operation panel 208, and it is determined whether the inspection ends by pressing of this inspection end button. Note that, in a case where there is no capture instruction (button pressing) in the determination at step S12 described above, the procedure shifts from step S12 to step S24. In this manner, steps S12 to S22 are repeatedly performed until the inspection by the moving image ends.

Thereafter, the lesion evaluation unit 220d obtains the spread of the lesion and the intensity of the lesion from the place information and the image evaluation value associated with the place information, and calculates the severity of the lesion on the basis of the spread of the lesion and the intensity of the lesion (step S26).

Finally, under the control of the system controller 202, the monitor 300 displays the calculated numerical value of the severity on the screen, or the printer 400 prints out the value of the severity (step S28).

In this manner, it is possible to acquire the capture instruction for acquiring the still image and the place information regarding the imaging place of the still image in response to the operation (pressing of the button) of determining one place out of the plurality of places in the lumen set in advance as the selected place as a trigger, so that it is possible to provide the electronic endoscope system 1 excellent in usability for the user.

Note that, in the flow illustrated in FIG. 10, the capture instruction for acquiring the still image and the place information regarding the imaging place of the still image are acquired by the pressing of the button displayed on the operation panel 208, but it is also possible to use the key of the keyboard 209 as illustrated in FIGS. 6(*a*) and 6(*b*) in place of the button displayed on the operation panel 208. In this case, the operation at step S10 is changed to an operation in which the display control unit 223 illustrated in FIG. 5 displays information in which the place information and each key of the keyboard 209 are associated with each other on the screen of the monitor 300. The display control unit 223 generates a control signal of the capture instruction and a signal of the place information corresponding to the key via the system controller 202 by pressing the key of the keyboard.

As described above, the selection of the selected place, the determination of the selected place, and the capture instruction may be performed in separate operations.

For the selection of the selected place, the determination of the selected place, and the capture instruction, in addition to the button and the key, it is possible to combine to use the user interface including the single switch such as the foot switch, the user interface that selects one selected place by switching the place information with the toggle switch or the toggle button, the user interface that performs the input operation by the mouse, the touch panel and the like by using the slider, the wheel and the like displayed on the operation panel 208 or the monitor 300, the user interface capable of selecting the operation content by detecting the direction in which the user's finger moves on the operation panel as the flick input used in the smartphone or the like.

The electronic endoscope system of the present invention is described above in detail, but the electronic endoscope system of the present invention is not limited to the above-described embodiment, and may of course be modified or changed variously within the scope and spirit of the present invention.

REFERENCE SIGNS LIST

1 Electronic endoscope system
100 Electronic scope
102 LCB
104 Light distribution lens
106 Objective lens
108 Solid-state image sensor
108a IR cut filter
108b Color filter
112 Driver signal processing circuit
114 Memory
200 Processor for an electronic endoscope
208a, 208b, 208c, 208d, 208e Button
209 Keyboard
220 Image processing unit
220a Image processing main unit
220b Still image acquisition unit
220c Association processing unit
220c1 Association processing main unit
220c2 Information correction unit
220d Lesion evaluation unit
220d1 Image evaluation unit
220d2 Spread evaluation unit
220d3 Lumen evaluation unit
222 UI control unit
223 Display control unit
230 Light source unit
300 Monitor
400 Printer

The invention claimed is:

1. An electronic endoscope system configured to acquire a still image from a moving image of living tissue imaged in a lumen, the electronic endoscope system comprising:
an electronic endoscope configured to image an image of living tissue in a lumen as a moving image;
a memory;
a processor configured to
acquire a part of an imaged moving image of the living tissue as a still image by an instruction,
record the still image in the memory, and
associate place information regarding an imaging place of the living tissue in the lumen with the still image;
a monitor configured to display the moving image and the still image; and
an operation panel configured to
transmit a capture instruction for acquiring the still image from the moving image to the processor in response to an operation performed on the operation panel of determining one place out of a plurality of places in the lumen set in advance as a selected place as a trigger, and
transmit information of the selected place to the processor as the place information regarding the imaging place during an imaging period of the moving image, wherein
the operation panel is provided with a plurality of buttons to which information of different places in the lumen is assigned so as to be distinguishable from each other, and is configured to determine the selected place by pressing of one of the buttons, and make the pressing of one of the buttons the trigger for transmission of the capture instruction.

2. The electronic endoscope system according to claim 1, wherein
in each of the buttons, a name of a place in the lumen, a distance from an open end of the lumen, or identification information specifying the place of the lumen is set as information of the place in the lumen.

3. The electronic endoscope system according to claim 2, wherein
the operation panel includes a touch panel, and
the button is a button in which the name of the place in the lumen, distance information from the open end of the lumen, or the identification information is displayed on the touch panel as the information of the place in the lumen.

4. The electronic endoscope system according to claim 1, wherein
the operation panel is a keyboard,
the button is a key of the keyboard, and
the processor is configured to control the monitor to display information in which the information of the place in the lumen set in the key is associated with a number, a character, or a symbol set in the key on the monitor.

5. The electronic endoscope system according to claim 1, wherein
the operation panel is provided with a selection operation device configured to select the selected place, and a determination operation device configured to determine the selected place that is selected, and is configured to transmit information of the selected place that is determined to the processor and transmit the capture instruction to the processor in response to a determination operation by the determination operation device as a trigger.

6. The electronic endoscope system according to claim 1, wherein the processor is configured to write the place information regarding the imaging place in the still image.

7. The electronic endoscope system according to claim 1, wherein
the still image is an image acquired in each of a plurality of different places in the lumen, and
the processor is configured to:
calculate an image evaluation value indicating intensity of a lesion of the living tissue in the still image on the basis of a pixel value of the still image;
obtain spread information of the lesion in a depth direction in the lumen by using place information regarding the imaging place associated with the still image in each of a plurality of places in the lumen and the image evaluation value of the still image in each of the plurality of places in the lumen; and
evaluate severity of the lesion in the lumen on the basis of the image evaluation value in each of the plurality of places in the lumen and the spread information of the lesion.

8. An electronic endoscope system configured to acquire a still image from a moving image of living tissue imaged in a lumen, the electronic endoscope system comprising:
an electronic endoscope configured to image an image of living tissue in a lumen as a moving image;
a memory;
a processor configured to
acquire a part of an imaged moving image of the living tissue as a still image by an instruction,
record the still image in the memory, and
associate place information regarding an imaging place of the living tissue in the lumen with the still image;
a monitor configured to display the moving image and the still image; and
an operation panel configured to
transmit a capture instruction for acquiring the still image from the moving image to the processor in response to an operation performed on the operation panel of determining one place out of a plurality of places in the lumen set in advance as a selected place as a trigger, and
transmit information of the selected place to the processor as the place information regarding the imaging place during an imaging period of the moving image,
wherein the processor is configured to overwrite the place information regarding the imaging place already associated with the still image with information of one place selected from the plurality of places in the lumen set in advance as the place information regarding the imaging place outside an imaging period of the moving image for a still image to which the place information regarding the imaging place is associated as erroneous information.

9. An electronic endoscope system configured to acquire a still image from a moving image of living tissue imaged in a lumen, the electronic endoscope system comprising:
an electronic endoscope configured to image an image of living tissue in a lumen as a moving image;
a memory;
a processor configured to
acquire a part of an imaged moving image of the living tissue as a still image by an instruction,
record the still image in the memory, and
associate place information regarding an imaging place of the living tissue in the lumen with the still image;
a monitor configured to display the moving image and the still image; and
an operation panel configured to
transmit a capture instruction for acquiring the still image from the moving image to the processor in response to an operation performed on the operation panel of determining one place out of a plurality of places in the lumen set in advance as a selected place as a trigger, and
transmit information of the selected place to the processor as the place information regarding the imaging place during an imaging period of the moving image, wherein
the operation panel is provided with a plurality of buttons to which information of different places in the lumen is assigned so as to be distinguishable from each other, and
the processor is configured to, by pressing one of the buttons of the operation panel, overwrite the place information regarding the imaging place already associated with the still image with information of a place in the lumen assigned to the pressed button as the place information regarding the imaging place.

* * * * *